United States Patent [19]

Skraba

[11] 4,162,273
[45] Jul. 24, 1979

[54] ALKALINE TREATMENT OF LIQUID PROPANE CONTAINING HF

[75] Inventor: Frank W. Skraba, Sweeny, Tex.

[73] Assignee: Phillips Petroleum Company, Bartlesville, Okla.

[21] Appl. No.: 868,364

[22] Filed: Jan. 10, 1978

[51] Int. Cl.² ............ C07C 9/14; C10G 19/02
[52] U.S. Cl. .................... 585/854; 208/285; 62/24; 62/28; 585/719; 585/802; 585/955
[58] Field of Search .......... 260/676 R, 683.48, 683.41, 260/683.42; 208/206

[56] References Cited
U.S. PATENT DOCUMENTS

| | | | |
|---|---|---|---|
| 2,487,142 | 11/1949 | Kelley | 260/676 R |
| 2,773,920 | 12/1956 | Vautrain et al. | 260/683.42 |
| 3,206,390 | 9/1965 | Van Pool | 260/683.41 |
| 3,449,239 | 6/1969 | Moore | 208/206 |

Primary Examiner—George Crasanakis

[57] ABSTRACT

Liquid propane containing HF is admixed in an eductor or sparger with aqueous alkaline solution, e.g., 2-5 percent aqueous NaOH maintained in a treating vessel, the eductor or sparger being located within a body of said alkaline treating agent in said vessel, thus to avoid explosion.

6 Claims, 1 Drawing Figure

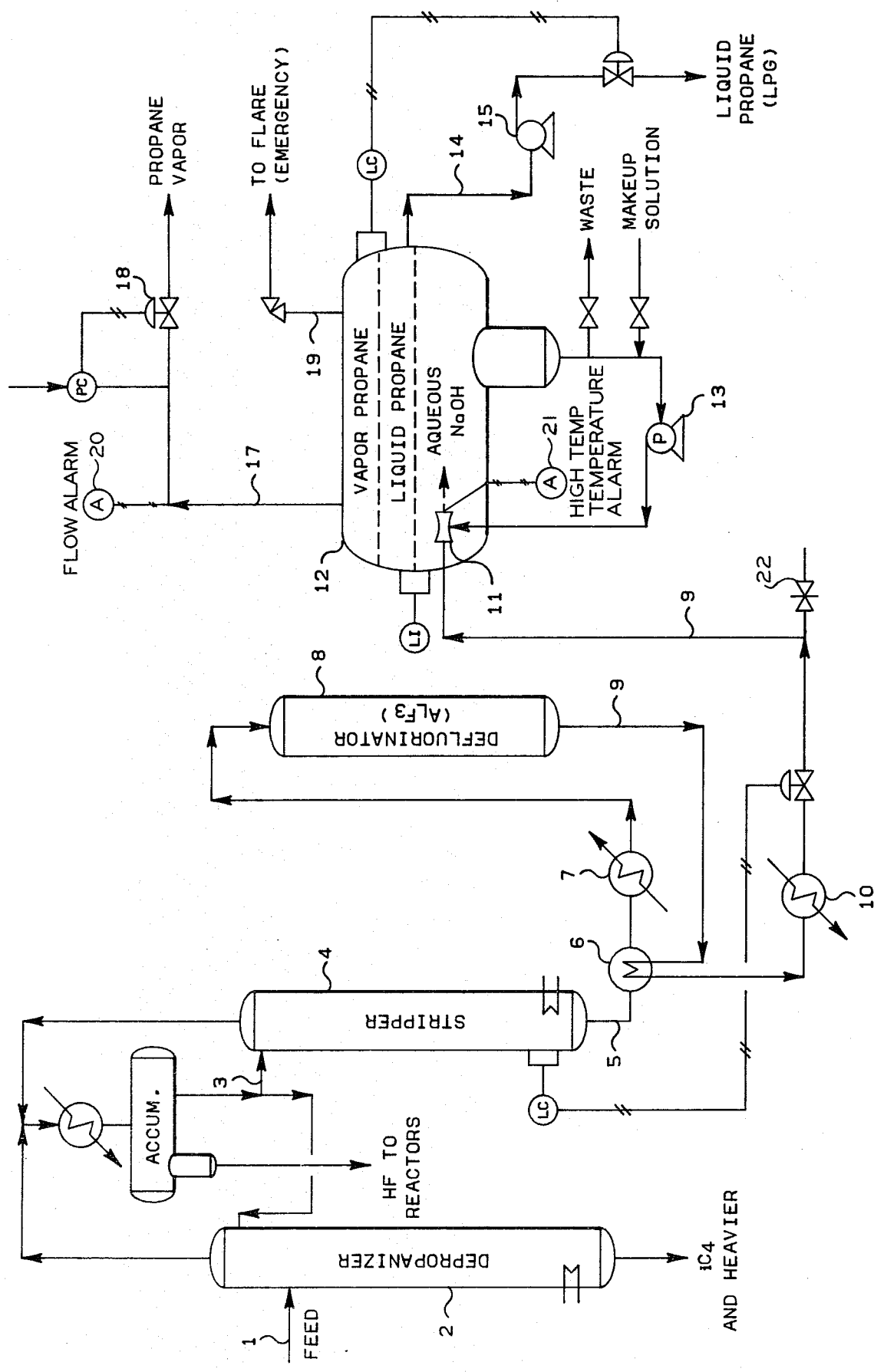

ALKALINE TREATMENT OF LIQUID PROPANE CONTAINING HF

This invention relates to the treatment of an HF-containing propane stream. In one of its aspects it relates to treating such a stream which has been subjected to HF stripping and to a defluorination operation in which organic fluorides are converted to other compounds and HF.

In one of its concepts the invention provides a method for treatment which comprises admixing aqueous alkaline treating agent, e.g., a 2–5 percent NaOH solution with the propane containing HF at a locus within a body of said alkaline treating agent as in an eductor or sparger located within a relatively large body of said alkaline treating agent, thus to absorb quickly and effectively sudden releases of heat which may be occasioned by surges of HF in the propane stream. In another of its concepts the invention locates the alkaline treating agent within a vessel or zone and maintains a phase of liquid propane thereabove. In a still further concept of the invention above the propane phase there is maintained a vapor space to accommodate the vaporous propane, especially as may be formed when propane is boiled from the liquid phase whenever sudden surges of heat resulting from sudden surges of HF and HF reaction with said alkaline treating agent is generated.

In U.S. Pat. No. 3,254,137, issued May 31, 1966, J. F. Hutto et al, there is described the use of solid KOH in a caustic treater wherein propane is treated.

In the operation of a propane treater containing a caustic in the form of solid KOH upon sudden surges of HF in the propane the sudden heat release experienced has caused explosion.

It is an object of this invention to provide a method or procedure for treating propane containing HF to remove the HF therefrom. It is another object of this invention to provide a method for neutralizing HF contained in propane while avoiding explosion which may occur due to sudden generation of heat. It is a further object of this invention to provide a method or procedure for treating HF containing propane with an alkaline treating agent, the procedure comprising a step or steps such that heat suddenly generated will be effectively absorbed or dissipated thus avoiding explosion.

Other aspects, concepts, objects, and the several advantages of the invention are apparent from a study of this disclosure, the drawing, and the appended claims.

According to the present invention, there is provided a treatment of propane containing HF, resulting from an alkylation operation in which HF catalyst is employed, which has been subjected to an HF stripping, to remove HF therefrom, and to a defluorination operation to decompose organic fluorides therein contained to other compounds and to HF, the step which comprises in a mixing section admixing intimately said stream with a small portion of aqueous alkaline treating agent adapted to neutralize the HF, said section being at a locus within a relatively large body of said treating agent. Further, according to the present invention, the mixing section is comprised within an eductor or sparger located well below the surface of a body of the treating agent as it is contained in a vessel the dimensions of which are considerably larger than that of the mixing section or eductor sparger.

Still further, according to the invention, for additional safety there is provided a liquid propane phase which is maintained above the alkaline aqueous treating agent or sodium hydroxide aqueous solution phase. Still further, there is maintained a vapor space above the liquid propane to allow for surges of vapor and concomitant increases of pressure which may occur when liquid propane is boiled off due to sudden generation of heat.

The conditions of operation of a depropanizer-HF stripping section in an alkylation of an isoparaffin with an olefin are well-known. They do not form a part of this invention. Further, the defluorination of an HF containing a stream, e.g., propane containing HF as in a defluorinator containing aluminum fluoride is also well-known.

The invention will now be described in connection with the drawing which shows a horizontally disposed vessel, having a keg, which creates a quiescent place in which to accumulate alkaline treating agent for use in an eductor as will now be described.

DESCRIPTION OF THE DRAWING

Referring now to the drawing, an alkylation effluent feed 1 is passed into depropanizer column 2. The depropanizer is operated in a now conventional manner with a cooler condenser and accumulator and return of HF catalysts to the reactors, a description of which is omitted for sake of brevity. The yield from the accumulator is passed by 3 into HF stripper 4 wherein HF is stripped from the propane withdrawn at 5 and passed by way of heat exchanger 6 and heater 7 to defluorinator 8 wherein organic fluorides are decomposed in the presence of a contact mass such as aluminum fluoride. The propane in which the organic fluorides have been decomposed, generating HF, is passed by 9 heat exchanger 6 and cooler 10 into eductor 11 which is actuated by an aqueous NaOH solution circulated from the keg of accumulator 12 by pump 13 into the eductor.

It is within the scope of the invention and the appended claims to use some other mixing or contacting device in addition to, or in lieu of, the eductor 11. For example, a sparger device or pipe can be installed in lieu of eductor 11. When such a pipe is installed, it is now preferred to have it extend along the bottom of accumulator 12 a length sufficient to permit rapid dissemination of any sudden larger than ordinary quantities of heat which may be generated when there is a surge in the quantity of HF being neutralized.

Propane liquid is pumped off at 14 by pump 15 to dryers operated in a now conventional manner, e.g., with bauxite to remove aqueous fluid and remove traces of acid. Propane vapor, especially vapor which may have been generated when there has been a sudden surge of HF causing unusual amount of heat is taken off at 17 through a pressure control valve 18.

For sake of ultimate safety a valve set to open at a predetermined pressure will permit unusual quantities of propane vapor to be passed to a flare by 19.

It will be seen that the three-phase operation of accumulator 12, i.e., vapor upon liquid and liquid upon the alkaline solution and the positioning of the eductor, or sparger, well within the body of aqueous NaOH provides an explosion-proof apparatus and operation, according to the invention.

The invention herein disclosed and claimed is considered to be an improvement over that disclosed and claimed in Ser. No. 868,363, filed Jan. 10, 1978, by Lucien H. Vautrain, the disclosure of which is incorporated herein by reference.

The following is a calculated example given by way of further disclosure to one skilled in the art of alkylation and treatment of streams emanating from such a plant especially from the depropanizer section thereof.

EXAMPLE

|  | Range | Specific |
|---|---|---|
| 5 Propane from HF Stripper 4: | | |
| Volume, B/H | (c) 10–60 B/H | 35 |
| Composition, Vol. % (a): | | |
| Propane, | (b) | 99.25 |
| Isobutane, | (b) | 0.75 |
| Organic Fluorides, | (c) up to 500 ppm (by wt.) | 25 |
| HF | (c) up to 50 ppm (by wt.) | 25 |

(a) Except as noted.
(b) Will vary, depending on source or plant operation.
(c) Can be very high during upsets, e.g., 0.5 to 1.0%.

| 9 Treated Stream from Defluorinator 8, and Feed to Caustic Washer 12: | | |
|---|---|---|
| Volume, B/H, | (e) 10–60 B/H | 35 |
| Composition, Vol. % (d): | | |
| Propane | (e) | 99.25 |
| Isobutane, | (e) | 0.75 |
| Organic Fluorides, nil | (f) | nil |
| HF, | (f) up to 100 ppm (by wt.) | 35 |

(d) Except as noted.
(e) Will vary, depending on source or plant operation.
(f) Can be very high during upsets, e.g., 0.5 to 1.0%.

| 13 Aqueous Caustic Solution to Washer 12: | | |
|---|---|---|
| Volume, B/H | (g) 10–60 B/H | 35 |
| Original NaOH, wt. %, | 2–5 | 4 |
| Final NaOH, wt. % |  | 2 |

(g) Will vary, depending on plant.

The system starts with about 4 wt. % NaOH in preferably demineralized water, or steam condensate, to minimize insoluble solids production from such as calcium in normal water which produces insoluble $CaF_2$. The caustic strength is kept below about 5 weight percent NaOH and above about 2 weight percent NaOH to insure that the produced NaF remains in solution in the reagent, and to insure that substantially complete removal of HF from the propane is effected. (NaF has a solubility of only about 4 grams per 100 cc of water at about 65° F.) Solids in the reagent can foul the eductor unit in vessel 40 and also have an adverse effect on the caustic pump.

|  | Range | Specific |
|---|---|---|
| (14) Propane Liquid Yield from Washer 12: | | |
| Volume, B/H | (h) 10–60 B/H | 35 |
| Composition, Vol. %, (i) | | |
| Propane, | (h) | 99.25 |
| Isobutane, | (h) | 0.75 |
| Organic Fluorides, | (j) nil | nil |
| HF, | nil | nil |

(h) Varies with plant.
(i) Except as noted.
(j) can be high if unit 8 is out.

Operating Conditions:

| 8 Defluorinator: | | |
|---|---|---|
| Temperature, °F. | 350–425 | 400 |
| Pressure, psig., | 180–270 | 250 |
| Contact time, seconds, | 10–60 | 35 |
| 12 Caustic Washer: | | |
| Temperature, °F. | 80–120 | 100 |
| Pressure, psig., | 160–190 | 175 |
| Propane/Caustic Solution | | |
| Liquid Volume Ratio, (k), | 0.8 to 1 – 1.2 to 1 | 1 to 1 |

(k) If a surge of HF enters unit 12, the heat generated by the reaction of HF with NaOH in the aqueous solution will be absorbed by the aqueous solution and thusly will prevent vaporization of liquid propane and explosion and fire which has occurred when a surge of HF entered the solid KOH treater and liquid propane, at about its bubble point, absorbed the heat of reaction.

A vapor flow rate alarm 20 and/or a high temperature alarm 21 can be used so that an operator can take corrective actions when upset flow of HF occurs. Such corrective action can include the return of flow 9 via 22 to the alkylation unit settler, not shown.

Reasonable variation and modification are possible within the scope of the foregoing disclosure, the drawing, and the appended claims, to the invention the essence of which is that HF containing propane from a depropanizer-stripping-defluorination operation is admixed with alkaline solution adapted to effectively neutralize HF in an eductor or equivalent means located within a body of such solution thereby assuring that only a relatively small quantity of HF can cause generation of heat and that such relatively small quantity is within the large body of aqueous solution of treating agent adapted to absorb sudden releases of heat and that in a described modification of the invention there is maintained above the layer of alkaline solution a liquid propane and a vapor propane phase.

I claim:

1. In the treatment of propane-containing stream resulting from an alkylation operation in which HF catalyst is employed and in which said stream has been subjected to an HF stripping to remove HF therefrom and to a defluorination step to decompose organic fluorides to form HF, the invention which comprises admixing said stream with a small portion of an aqueous alkaline treating agent in a mixing section to neutralize HF, said section being at a locus within a relatively large body of said treating agent.

2. A treatment according to claim 1 wherein said large body of treating agent is in a zone which also contains above said treating agent a liquid propane phase.

3. A treatment according to claim 2 wherein there is above the liquid propane a space containing vapor.

4. A treatment according to claim 1 wherein the mixing section comprises an eductor.

5. A treatment according to claim 1 wherein the mixing section comprises a sparger.

6. A treatment according to claim 5 wherein the sparger extends along the bottom of said relatively large body of said treating agent.

* * * * *